US010928525B2

(12) United States Patent
Kwon et al.

(10) Patent No.: US 10,928,525 B2
(45) Date of Patent: Feb. 23, 2021

(54) INTEGRATED MONITORING SYSTEM FOR RADIOLOGICAL SURVEILLANCE OF GROUNDWATER AND OPERATION METHOD THEREOF

(71) Applicant: KOREA ATOMIC ENERGY RESEARCH INSTITUTE, Daejeon (KR)

(72) Inventors: Jang-Soon Kwon, Goyang-si (KR); Yong-Kwon Koh, Daejeon (KR); Jae-Kwang Lee, Daejeon (KR); Min-Hoon Baik, Daejeon (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 116 days.

(21) Appl. No.: 16/211,965

(22) Filed: Dec. 6, 2018

(65) Prior Publication Data
US 2020/0025949 A1 Jan. 23, 2020

(30) Foreign Application Priority Data
Jan. 24, 2018 (KR) .................. 10-2018-0008946

(51) Int. Cl.
  *G01T 1/167* (2006.01)
  *G01T 1/169* (2006.01)
  *G01N 33/24* (2006.01)
(52) U.S. Cl.
  CPC .............. *G01T 1/167* (2013.01); *G01T 1/169* (2013.01); *G01N 33/246* (2013.01)
(58) Field of Classification Search
  CPC ........ G01T 1/167; G01T 1/169; G01N 33/246
  (Continued)

(56) References Cited

U.S. PATENT DOCUMENTS 6,865,933 B1 * 3/2005 Einarson ............... E21B 33/122
  166/264
2018/0294064 A1 * 10/2018 Downey ................. E21B 49/00

FOREIGN PATENT DOCUMENTS

JP 2002-273405 A 9/2002
JP 2002-350369 A 12/2002
(Continued)

OTHER PUBLICATIONS

Translation of JP-2014232047-A (Year: 2014).*
(Continued)

*Primary Examiner* — Nathaniel T Woodward
(74) *Attorney, Agent, or Firm* — Scully Scott Murphy and Presser (57) ABSTRACT

An integrated monitoring system for radiological surveillance of groundwater and an operation method thereof are disclosed. The integrated monitoring system for radiological surveillance of groundwater around a nuclear facility according to an embodiment of the present disclosure may include a field monitoring system configured to monitor sectionally isolated groundwater characteristics by establishing a multiple packer system at each depth in groundwater around the nuclear facility, and measure whether or not radioactive contamination has occurred at each depth in groundwater pumped through an automatic branching apparatus connected to a sectional groundwater flow pipe isolatedly disposed at the each depth, and convert field measurement data acquired based on the measurement result into a DB and transmit the DB to a remote monitoring apparatus over a network, and the remote monitoring apparatus configured to remotely control the field monitoring system, and receive the DB-based field measurement data from the field monitoring system, and analyze the received field measurement data to predict a radioactive contaminant source, and (Continued)

provide a contaminant plume showing the distribution characteristics of contaminants in 3D graphic processing.

9 Claims, 9 Drawing Sheets

(58) Field of Classification Search
USPC .................................................. 73/40.5 R
See application file for complete search history.

(56) References Cited

FOREIGN PATENT DOCUMENTS

| JP | 2004-150968 | A | | 5/2004 |
|---|---|---|---|---|
| JP | 2005-049148 | A | | 2/2005 |
| JP | 4250876 | B2 | | 4/2009 |
| JP | 2009-162502 | A | | 7/2009 |
| JP | 2013-104194 | A | | 5/2013 |
| JP | 2013104194 | A | * | 5/2013 |
| JP | 2014-021074 | A | | 2/2014 |
| JP | 2014-232047 | A | | 12/2014 |
| JP | 2014-232435 | A | | 12/2014 |
| JP | 2014232047 | A | * | 12/2014 |
| JP | 2016-065787 | A | | 4/2016 |
| KR | 100799602 | B1 | | 2/2008 |
| KR | 2013-0096074 | A | | 8/2013 |
| KR | 1020130055177 | B1 | | 8/2014 |
| KR | 1020140115779 | A | | 10/2014 |
| KR | 2020160002889 | U | | 8/2016 |

OTHER PUBLICATIONS

Translation of JP-2013104194-A (Year: 2013).*
Notice of Reasons for Refusal dated Feb. 4, 2020 received in Japanese Patent Application No. JP 2018-234361 together with an English language translation.

* cited by examiner

Multi-Level Well Transect

INTEGRATED MONITORING SYSTEM FOR RADIOLOGICAL SURVEILLANCE OF GROUNDWATER AND OPERATION METHOD THEREOF

CROSS-REFERENCE TO RELATED APPLICATIONS

Pursuant to 35 U.S.C. § 119(a), this application claims the benefit of earlier filing date and right of priority to Korean Application No. 10-2018-0008946, filed on Jan. 24, 2018, the contents of which is incorporated by reference herein in their entirety.

BACKGROUND OF THE INVENTION

1. Field of the Invention

The present disclosure relates to an integrated monitoring system for radiological surveillance of groundwater and an operation method thereof.

2. Description of the Conventional Art

At present, nuclear power plants with longer than 30 years of operation in the world have exceeded 50% of the total, and have entered the nuclear aging stage in earnest. Until recently, groundwater contamination by unplanned release of radioactive materials has been identified in more than 50% of closed nuclear power plants and operational nuclear power plants in the United States.

Radioactive contamination of groundwater has a direct effect on the human body as well as long-term and persistent effects on the human body and ecosystem due to the internal exposure caused by the ingestion of agricultural and livestock products. In addition, it takes a long time to clean up contamination, and even if the contamination is cleaned up, anxiety about the contaminated area can only be amplified due to the fear of radioactive contamination.

In addition, groundwater contamination by radioactive materials causes an increase in dismantling period, cost, and waste generation amount of closed nuclear power plants. Recently, in the United States, technical guidelines on groundwater protection programs and technical guides on the recovery of contaminated groundwater and contaminated soil have been prepared.

Therefore, periodical groundwater monitoring is required before and after the operation and decommissioning of the nuclear facilities, and integrated field monitoring technology development capable of monitoring radioactivity in groundwater simultaneously with hydrogeochemical data is required.

SUMMARY OF THE INVENTION

Accordingly, in order to solve the above tasks, an object of the present disclosure is to provide an integrated monitoring system for radiological surveillance of groundwater capable of collectively monitoring radioactive contamination in groundwater before and after the operation and decommissioning of nuclear facilities simultaneously with hydrogeochemical data, and predicting a contaminant plume in real time through radioactivity measurement data in groundwater, and an operation method thereof.

Furthermore, another object of the present disclosure is to provide an integrated monitoring system for radiological surveillance system capable of remotely monitoring radioactive contamination at each depth in groundwater in real time, and three-dimensionally diagnosing the distribution and transport of the predicted contaminant plume to provide a graphic, and an operation method thereof.

Accordingly, in order to solve the foregoing tasks, an integrated monitoring system for radiological surveillance of groundwater around a nuclear facility according to an embodiment of the present disclosure may include a field monitoring system configured to establish a multiple packer system at each depth in groundwater around the nuclear facility to monitor sectionally isolated groundwater characteristics, and measure whether or not radioactive contamination has occurred at each depth in groundwater pumped through an automatic branching apparatus connected to a sectional groundwater flow pipe isolatedly disposed at the each depth, and convert field measurement data acquired based on the measurement result into a DB and transmit the DB to a remote monitoring apparatus over a network; and the remote monitoring apparatus configured to remotely control the field monitoring system, and receive the DB-based field measurement data from the field monitoring system, and analyze the received field measurement data to predict a radioactive contaminant source, and provide a contaminant plume showing the distribution characteristics of contaminants in 3D graphic processing.

Furthermore, a method of operating an integrated monitoring system for radiological surveillance of groundwater including a field monitoring system around a nuclear facility and a remote monitoring apparatus that controls the field monitoring system may include establishing a multiple packer system at each depth in groundwater around the nuclear facility to monitor sectionally isolated groundwater characteristics; measuring whether or not radioactive contamination of groundwater has occurred for the each section through an automatic branching apparatus connected to a groundwater flow pipe isolatedly disposed for the each section; converting field measurement data acquired on the basis of the measurement result into a DB and transmitting the DB to the remote monitoring apparatus over a network; analyzing the DB-based field measurement data from the field monitoring system to predict a radioactive contaminant source; and displaying a contaminant plume showing the distribution characteristics of contaminants in 3D graphic processing.

BRIEF DESCRIPTION OF THE DRAWINGS

The present disclosure will become more fully understood from the detailed description given herein below and the accompanying drawings, which are given by illustration only, and thus are not limitative of the present disclosure, and wherein.

DETAILED DESCRIPTION OF THE PREFERRED EMBODIMENTS

First, an integrated monitoring system for radiological surveillance of groundwater around a nuclear facility according to an embodiment of the present disclosure may include a field monitoring system installed in or around the nuclear facility and a remote monitoring apparatus for remotely controlling the same.

Furthermore, as various modifications can be made and diverse embodiments are applicable to the present disclosure, specific embodiments will be illustrated with reference to the accompanying drawings and described in detail. However, those specific embodiments should not be construed to limit the present disclosure, and should be construed as being extended to all modifications, equivalents, and substitutes included in the concept and technological scope of the invention.

It will be understood that although the terms first, second, etc. described herein may be used herein to describe various elements, these elements should not be limited by these terms. In other words, the terms are used merely for the purpose to distinguish an element from the other element. For example, a first element may be named to a second element, and similarly, a second element may be named to a first element without departing from the scope of right of the invention. Furthermore, it will be understood that the term "and/or" includes any and all combinations of one or more of the associated listed items.

In addition, in case where an element is "connected" or "linked" to the other element, it may be directly connected or linked to the other element, but another element may be existed therebetween. In contrast, when an element is referred to as being "directly connected with" another element, there are no intervening elements present.

Furthermore, it should be noted that the terms used herein are merely used to describe a specific embodiment, but not to limit the present disclosure. Incidentally, unless clearly used otherwise, expressions in the singular number include a plural meaning. Terms "include" or "has" used herein should be understood that they are intended to indicate an existence of several components or several steps, disclosed in the specification, and it may also be understood that part of the components or steps may not be included or additional components or steps may further be included.

Moreover, unless defined otherwise, the terms used herein including technological or scientific terms have the same meaning that is generally understood by those ordinarily skilled in the art to which the invention pertains. The terms used herein shall not be interpreted not only based on the definition of any dictionary but also the meaning that is used in the field to which the invention pertains. Also, unless clearly defined, the terms used herein shall not be interpreted too ideally or formally.

Hereinafter, preferred embodiments of the present disclosure will be described in detail with reference to the accompanying drawings, and the same or similar components are designated with the same reference numerals regardless of the numerals in the drawings and their redundant description will be omitted.

The "nuclear facility", which is continuously referred to in the present disclosure, may broadly include a large-scale facility that uses actual monitoring target nuclides, and the like, and is concerned about the leakage of contaminants into groundwater and soil such as a nuclear power plant, a research reactor, a fuel manufacturing plant, a radioactive waste disposal site, and the like.

Figure 1:
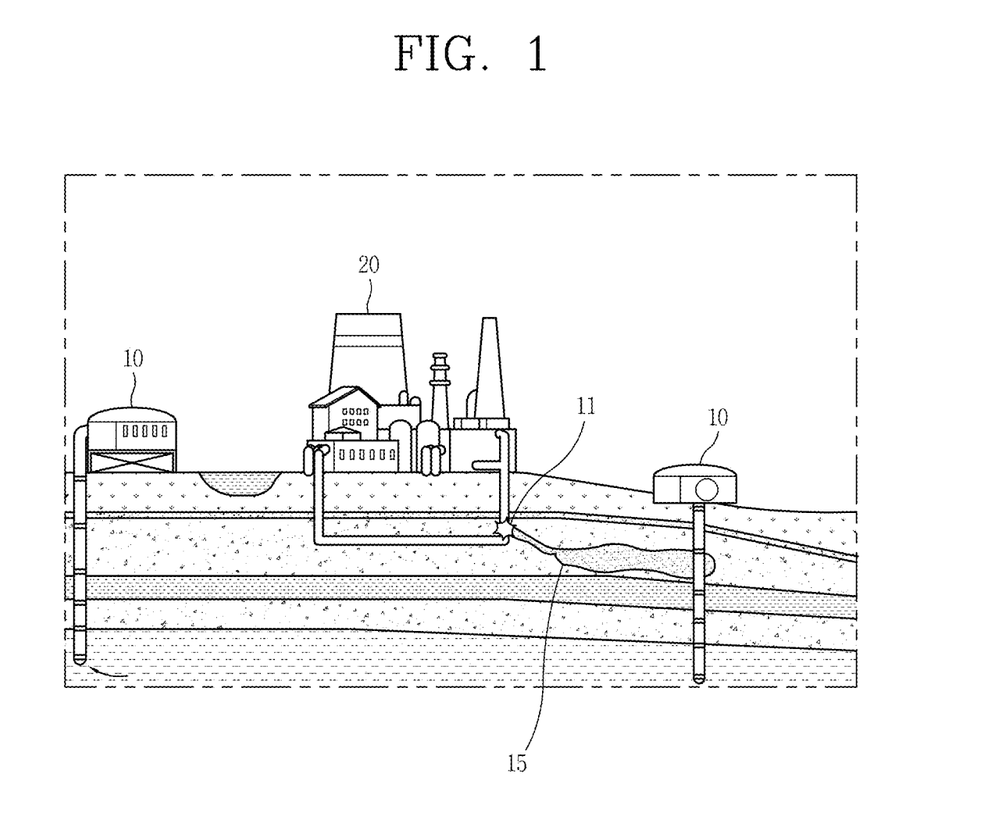
FIG. 1 is a conceptual view illustrating underground leakage of radioactive materials around a nuclear facility and resultant groundwater monitoring according to an embodiment of the present disclosure.

FIG. 1 is a conceptual view illustrating the leakage of radioactive materials in groundwater and groundwater monitoring around a nuclear facility according to an embodiment of the present disclosure. The position of a monitoring well 10 for monitoring groundwater radioactive contamination is determined based on a groundwater flow model deduced from a site concept model according to the survey of nuclear facility site characteristics.

Referring to FIG. 1, monitoring wells 10 should be divided into upstream and downstream according to the flow direction of groundwater around a nuclear facility 20, and installed at a minimum of two points. It is a required number for analyzing the behavior characteristics due to contaminants inflow into background water quality in the future. For example, when a pipeline buried and connected from the nuclear facility 20 is damaged, radioactive materials 15 flow out of the damaged point 11 and transport along the flow direction of groundwater. Therefore, in this case, such radioactive materials 15 may be measured in an isolated section of the monitoring well 10 illustrated on the right side in FIG. 1.

However, the present disclosure is not limited to the two monitoring wells, and three or more monitoring points may be installed and operated when it is required to detect the behavior of a contaminant plume more precisely and accurately.

In the related art, the installation of such a monitoring well does not reflect groundwater flow or is limited to acquiring radioactivity in groundwater collected in a non-isolated open borehole state on a quarterly basis, but in the present disclosure, a monitoring well according to groundwater flow is selected and a highly fractured section with fast groundwater flow in the monitoring well is sectionally isolated and monitored to prevent the effect of dilution, predict contaminant sources according to the types of measured radioactive materials, quickly determine the distribution of a contaminant plume, and provide a direct determination basis in establishing a restoration plan.

An integrated monitoring system for radiological surveillance of groundwater according to the present disclosure establishes a multiple packer system at each depth for groundwater around the nuclear facility to monitor groundwater characteristics for a groundwater flow path at each depth, and pump, branch and collect groundwater at each depth through an automatic branching apparatus connected to a groundwater flow pipe isolatedly disposed at each depth to measure whether or not radioactive contamination has occurred. When these measurements are repeated for every isolated depth in the well, the acquired field measurement data is converted into a database (DB) and the DB-based field measurement data is transmitted to a remote monitoring apparatus over the network. At this time, the DB-based field measurement data includes a head pressure, a simple water quality, radioactivity measurement data and the like for each section. Then, the remote monitoring system performs a time series analysis of the DB-based field measurement data to calculate numerical values related to an groundwater flow model, a geochemical model, and a nuclide transport model. Then, the remote monitoring system predicts radiative contaminant sources based on the calculated numerical values, and displays a contaminant plume in 3D graphic processing based on a groundwater flow model showing the distribution and transport characteristics of contaminants.

Figure 2:
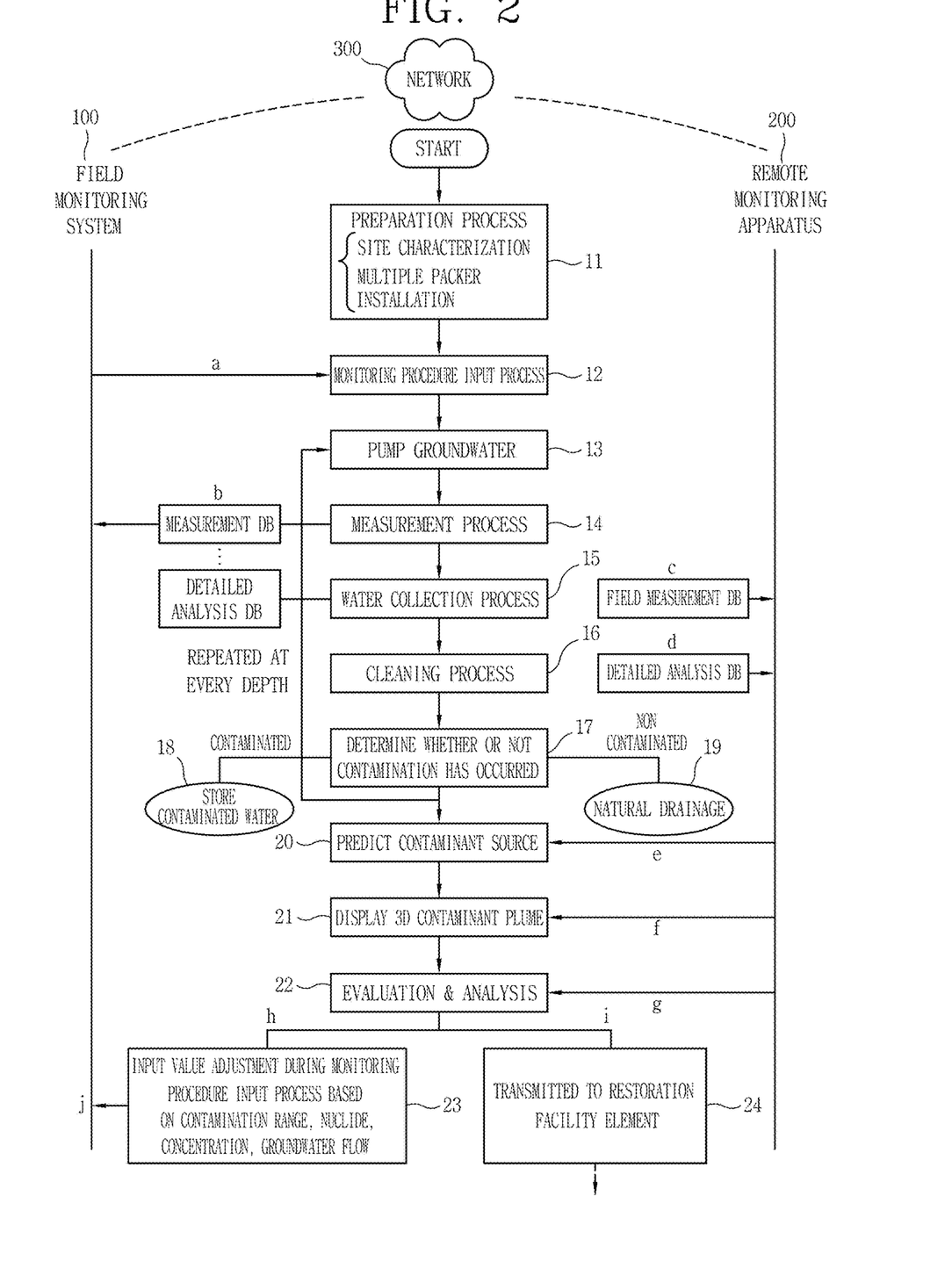
FIG. 2 is a flowchart for explaining an operation procedure of groundwater monitoring according to an interaction between a field monitoring system and a remote monitoring apparatus in an integrated monitoring system for radiological surveillance of groundwater according to an embodiment of the present disclosure.

FIG. 2 is a flowchart for explaining an operation procedure of groundwater monitoring according to an interaction between a field monitoring system and a remote monitoring apparatus in an integrated monitoring system for radiological surveillance of groundwater according to an embodiment of the present disclosure.

Referring to FIG. 2, in the integrated monitoring system for radiological surveillance of groundwater, a field monitoring system 100 installed around the nuclear facility performs a groundwater monitoring operation while communicating with a remote monitoring apparatus 200 located remotely through a network.

The operation process of radioactive monitoring of groundwater by the integrated monitoring system for radiological surveillance of groundwater is as follows. Prior to monitoring groundwater radioactivity, preparation processes 11 such as a site characterization evaluation through a site survey around a nuclear facility, monitoring well locating and drilling, monitoring depth (zone) selection through a monitoring well hydrogeochemical survey, and multiple packer installation, and the like are carried out in advance.

Specifically, the preparation processes 11 may include 1) establishing a site conceptual model based on site characterization evaluation, 2) establishing an groundwater flow model and a geochemical model, 3) determining the location and depth of a monitoring well, 4) drilling, surveying, testing and interpreting the monitoring well, and 5) periodically hydrogeochemical monitoring.

The reason why site characterization evaluation should be preceded is because the underground behavior of radioactive contaminants released from a nuclear facility is dependent on the hydrogeological and geochemical characteristics of the nuclear facility site. In other words, groundwater flow and hydrogeochemical characteristics may be evaluated and predicted only since site characterization is preceded. Then, the types of radioactive materials in the nuclear facility and the positions of potential contaminant sources are evaluated, and the locations and depths of the monitoring wells are selected based on a groundwater flow model, and accordingly, real-time monitoring of radioactive contamination in groundwater is carried out. Therefore, it is necessarily required to evaluate site characteristics and detect facility components as a preceding process of groundwater radioactive contamination monitoring according to the present disclosure.

Furthermore, in the present disclosure, an isolated section at each depth for a main groundwater flow path is formed using a multiple packer system into a monitoring well. In this manner, a section for a main groundwater flow path may be separated using multiple packers to accurately detect the behavior of the contaminant plume. The structure and specific description of multiple packers included in a multiple packer system will be described in more detail with reference to FIGS. 5A and 5B.

Referring to FIG. 2, subsequent to the preparation process 11, a monitoring procedure input process 12 is carried out through the field monitoring system 100 or the remote monitoring apparatus 200 (although not shown) (a). For example, a radioactive measurement cycle of groundwater for each section, a collection cycle of measurement data, a groundwater collection cycle and a water collection amount may be set through an input element of the field monitoring system 100.

In addition, the setting of a network communication cycle between the field monitoring system 100 and the remote monitoring apparatus 200 may be included in the monitoring procedure input process 12 as well. Moreover, a laboratory analysis cycle in the field monitoring system 100 may also be included in the monitoring procedure input process 12.

When the monitoring procedure is entered (12), automatically branched groundwater at a selected specific depth is pumped out (13), and measurement is carried out (14). In addition, the automatic branched groundwater is collected (15), and then the cleaning process for the flow tube and measurement chamber is carried out (16).

Then, it is determined whether or not groundwater collected during the measurement process 14 is contaminated (17). As a result of the determination, when it is contaminated groundwater, the contaminated water is stored (18). Otherwise, natural drainage is carried out (19). The process of groundwater pumping, measurement, collection, cleaning, and drainage described above is repeated until all multiple depths in groundwater are completed.

Specifically, in accordance with the execution of the entered monitoring procedure, an groundwater automatic branching unit 120 (FIG. 3A) and an groundwater pump unit 110 (FIG. 3A) operate. The pumped groundwater 13 moves to a measurement chamber unit 130 (FIG. 3A), and physicochemical water quality measurement and radioactivity measurement in groundwater are carried out according to the initially entered monitoring procedure 12.

At this time, measurement data collected during the measurement process 14 is converted into a database in the field monitoring system 100 (b). At the same time, measurement values of various sensors embedded in the multiple packer system are converted into a database in real time.

A groundwater sample collected during the collection process 15 may be automatically collected into a container designed for a planned volume of the sample through an automatic sample collection unit 140 for a laboratory precise analysis. In addition, the result of a laboratory precise analysis is converted into a detailed analysis database. In one embodiment, a result of the laboratory precise analysis may be compared with field measurement values to improve or maintain the sensitivity, accuracy, and precision of the field measuring instrument.

The detailed analysis DB is used in conjunction with the measurement DB (b), and they are periodically updated in the remote monitoring apparatus 200 (c, d).

Thus, when the pumping, measurement, and drainage of groundwater at a specific depth selected for a planned time period or a planned measurement cycle are completed, the groundwater automatic branching unit 120 operates according to a planned input procedure (or inputted monitoring procedure). At this time, the cleaning of the measurement cell and the chamber is carried out with the pumped groundwater (16).

When the pumping, measurement, collection, cleaning, and drainage at all multiple depths in groundwater are completed, the field monitoring system 100 transmits the field measurement data DB to the remote monitoring apparatus 200 at a planned communication cycle.

As a result, the remote monitoring apparatus 200 may predict (20) radioactive contamination of groundwater and the position of a contaminant source in real time using a result of field measurement data even from a remote place (e). It is possible because the kinds of nuclides that occur according to unplanned release due to deterioration are shown differently for each nuclear facility system. Specifically, the remote monitoring apparatus 200 may predict groundwater flow and a radioactive contaminant plume through numerical calculations related to measurement data, a groundwater flow model, a geochemical model, and a nuclide transport model received in real time.

In addition, the remote monitoring apparatus 200 displays a 3D contaminant plume based on the prediction of a potential contaminant source. Here, in order to generate a 3D contaminant plume, position coordinate values for predicting contaminant sources and contamination strength may be stored in a DB 250 (FIG. 3B) within the remote monitoring apparatus 200, and a history of coordinate values changed according to the update of the DB 250 (FIG. 3B) is stored together with time information or in time order.

The history of coordinate values stored in the DB 250 (FIG. 3B) may be generated as a three-dimensional stereoscopic image, and visualized as a contoured three-dimensional stereoscopic image through a known mapping technique, that is, displayed through a display element 230.

In addition, such a contoured three-dimensional stereoscopic image may be displayed as a three-dimensional image in which a three-dimensional stereoscopic image moves to correspond to a groundwater flow model (including a predicted advection rate of a contaminant plume depending on the flow direction and flow rate of groundwater) calculated above as time passes. Therefore, it provides direct help to a restoration plan according to the type and distribution range of contaminants when radioactive contamination occurs in groundwater.

Then, the remote monitoring apparatus (g) evaluates and analyzes the displayed 3D contaminant plume (22), and then performs the following operation based on the evaluation.

For an operation, an input value of the monitoring procedure input process 12 may be adjusted based on a range of radioactive contamination, a nuclide transport, a contamination concentration, and a groundwater flow (23). For another operation, 3D contaminant plume display data is transmitted to a contamination restoration facility element (24).

Figure 3A:
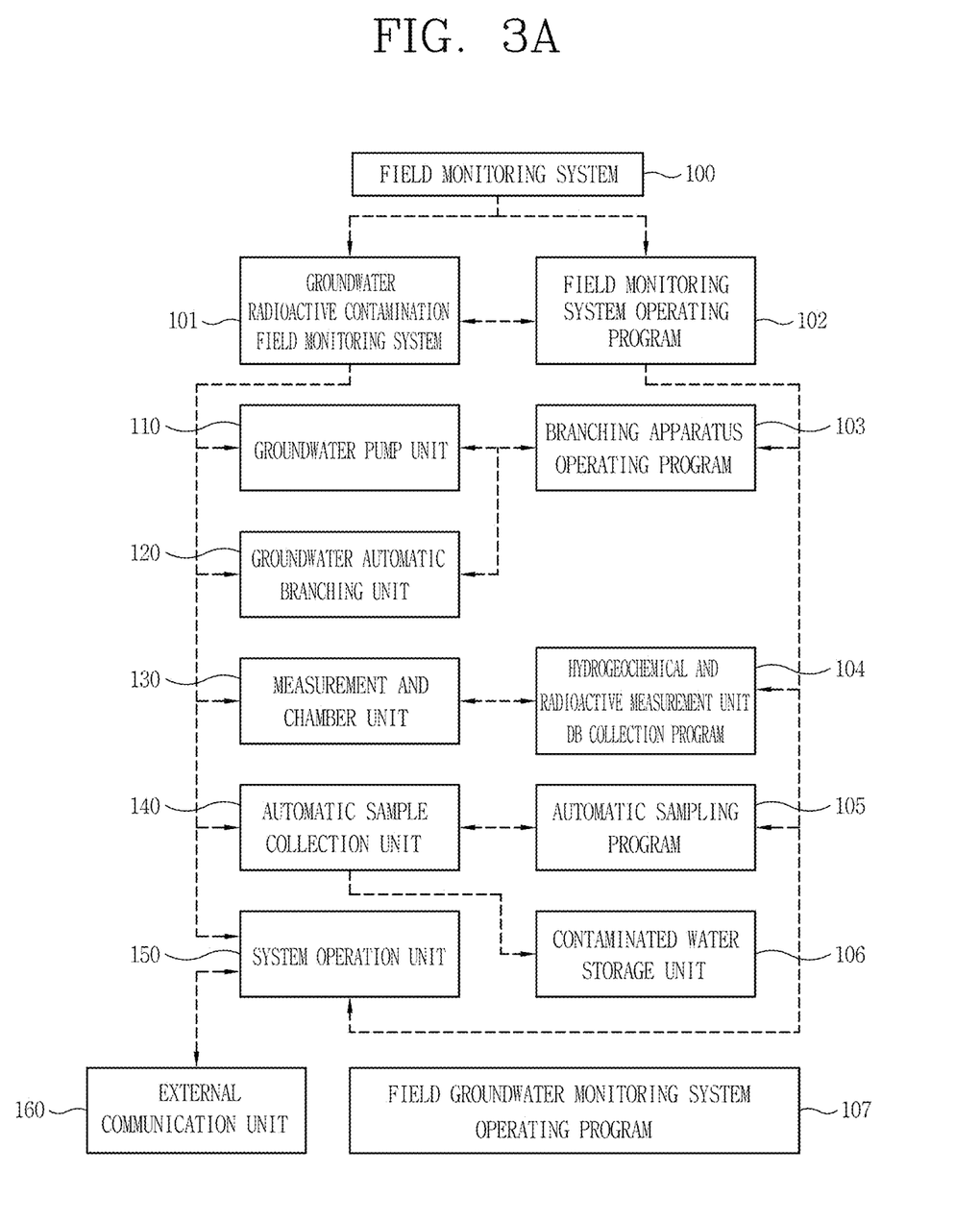
FIGS. 3A and 3B are block diagrams illustrating a field monitoring system and a remote monitoring apparatus in an integrated monitoring system for radiological surveillance of groundwater according to an embodiment of the present disclosure, respectively.
Figure 3B:
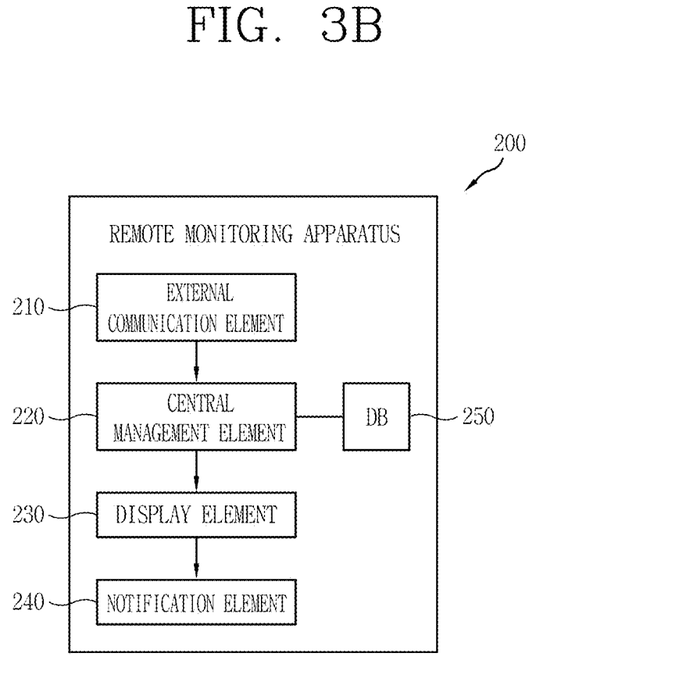

Hereinafter, FIGS. 3A and 3B are block diagrams for explaining the configuration of a field monitoring system and a remote monitoring apparatus constituting an integrated monitoring system for radiological surveillance of groundwater according to an embodiment of the present disclosure, respectively.

Referring first to FIG. 3A, the field monitoring system 100 implements and executes various software programs, i.e., field monitoring system operating programs 102, on a groundwater radioactive contamination field monitoring system 101 largely composed of hardware components to perform a field groundwater contamination monitoring operation.

The groundwater radioactive contamination field monitoring system 101 includes a groundwater pump unit 110, a groundwater automatic branching unit 120, a measurement chamber unit 130, an automatic sample collection unit 140, a contaminated water storage unit 106, a system operation unit 150, and an external communication unit 160.

Furthermore, the field monitoring system operating program 102 may include a branching apparatus operating program 103, a hydrogeochemical and radioactive measurement unit DB collection program 104, an automatic sampling program 105, and a field groundwater monitoring system operating program 107.

In addition, although not shown, the field monitoring system 100 includes a warehouse, which is a laboratory embedded with field monitoring system configurations including a monitoring well ground exposed section, and a multiple packer system installation monitoring well within the warehouse. It will be described in more detail below with reference to FIG. 6A.

The groundwater pump unit 110 includes a groundwater flow pipe at each depth of a multiple packered monitoring well connected to a metering pump and the groundwater automatic branching unit 120. Here, since one groundwater flow pipe is connected to the groundwater pump unit 110, one groundwater pump is sufficient in the field monitoring system 100. A groundwater flow meter, a sensor or the like may be installed in the relevant groundwater flow pipe to check whether or not groundwater is properly pumped.

The groundwater automatic branching unit 120 is an apparatus for connecting groundwater flow pipes from isolated sections at multiple depths to pump and collect only groundwater in a depth section suitable for the purpose of the survey. For example, the groundwater automatic branching unit 120 according to the present disclosure may be an apparatus to which a rotary manifold system using a 3-way valve or a stepping motor is applied.

The measurement chamber unit 130 includes a physicochemical water quality measuring instrument and a radioactivity measuring instrument in groundwater. In general, for physicochemical water quality measurement, measurements are made by inserting pH, ORP (oxidation-reduction potential), DO (dissolved oxygen) sensors and the like into the flow cell (chamber) to disallow each sensor to be affected by the outside air. Furthermore, if an EC (electrical conductivity) sensor is not installed in the monitoring well, the physicochemical water quality measurement may be performed by inserting them into the relevant flow cell. In addition, the turbidity of the groundwater quality factors may be measured by the relevant measuring unit.

Radioactivity measurements include the driving of beta-ray source and gamma-ray source measuring instruments. Sample injection, cocktail supply and mixing for the measurement of beta-ray sources are carried out by automation. A groundwater radioactivity measurement chamber for gamma-ray source measurement is designed differently according to the shape of a gamma-ray source measurement sensor, and a shielding material (for example, lead, etc.) of about 10 cm or more is wrapped around an outside of the chamber to block the effect of external radioactivity. However, this is merely an embodiment.

The automatic sample collection unit 140 is a system for acquiring samples in the field for a quantitative analysis of the quality of groundwater (inorganic component analysis, stable isotope analysis, radioisotope analysis, etc.), and designed to move later to a laboratory for precise analysis. The design of the automatic sample collection unit 140 is made in consideration of the amount of sample required for each analysis item, and the type and size of a sample storage container are determined according to the design.

A groundwater sample that does not have abnormality in radioactivity measurement or that does not exceed a discharge allowance standard are automatically drained, and contaminated groundwater is additionally stored in the contaminated water storage unit 106. A shielding system is applied to an outside of the contaminated water storage unit 106, and its own criteria is additionally provided and operated for a contaminated water treatment system.

The system operating unit 150 includes a field management element including various operating programs (a groundwater pumping program, a branching apparatus operating program, a measurement DB collection program, an automatic sample collection program, a DB transmission program, etc.) and an external communication element 160 connected thereto.

The field management element is controlled by a central management element 220 of the remote monitoring apparatus 200. The external communication element 160 may be operated using any one of LAN, CDMA, and LTE modes according to the purpose of the user and a field situation, and may include two or more communication elements to prevent the loss of data.

In one embodiment, a measurement cycle of the monitoring of the groundwater characteristics may be determined by a monitoring procedure input value entered through the field monitoring system 100 or the remote monitoring apparatus 200. In such a case, the field monitoring system 100 may automatically adjust the monitoring procedure input value based on at least one of a radioactive contamination range, a concentration, a groundwater flow, and a radioactive nuclide included in a 3D stereoscopic image displayed by the display element 230 of the remote monitoring apparatus 200.

Next, referring to FIG. 3B, the remote monitoring apparatus 200 constituting the groundwater monitoring system includes an external communication element 210, a central management element 220, a DB 250, a display element 230, and a notification element 240.

The external communication element 210 is an element for communicating with the field monitoring system 100 and an external facility system (e.g., external restoration system).

The central management element 220 is connected to the external communication element 210 to analyze field measurement data received from the field monitoring system 100 and generate a control command for remotely controlling the field management element of the system 100 on the basis of the analysis result.

The DB 250 is connected to the central management element 220 to store field measurement data received from the field monitoring system 100 and the analysis data of the field measurement data. At this time, the stored data may include coordinate values of the positions of the predicted contaminant sources and tabulated coordinate values that vary according to the groundwater flow model.

The display element 230 is connected to the central management element 220 to display the field measurement data and analysis data stored in the DB 250 in three-dimensional graphic modeling. Furthermore, the display element 230 visualizes and provides the distribution characteristics of nuclides from potential contaminant sources including groundwater flow in the nuclear facility site in real time. In addition, the display element 230 may display two-dimensional data corresponding to a time series analysis, a groundwater flow model, a geochemical model, and a nuclide transport model in real time.

Moreover, the central management element 220 provides the automatic adjustment of the monitoring procedure to the field monitoring system based on the analysis result of the display element 230.

Furthermore, in one embodiment, the external communication element 210 may include a plurality of communication network elements to prevent the loss of data. In this case, the DB-based measurement data is received from the field monitoring system 100 for a planned communication cycle using any one of a plurality of communication network elements, and data corresponding to the calculated numerical values and the three-dimensional graphic modeling is transmitted to the field monitoring system 100 using another one thereof.

In addition, the three-dimensional graphic model outputted through the display element 230 may be displayed in a single three-dimensional image format combined with a radioactive contamination range, a concentration, a groundwater flow, and a nuclide transport in the monitored groundwater.

Furthermore, in one embodiment, the central management element 220 may include an input element (not shown) for receiving a time setting related to the three-dimensional graphic model. Thus, moving three-dimensional graphic modeling may be displayed to gradually change the combined image representing the range of contamination, concentration, flow of groundwater, and nuclide transport according to the received time setting. It may be used as an element for predicting a future transport of radioactive contaminants in groundwater.

In addition, in one embodiment, the central management element 220 may communicate with an external restoration system through the external communication element 210. Specifically, based on a radioactive contamination evaluation 22 (FIG. 2) corresponding to a contaminant plume analysis result, the displayed three-dimensional graphic model and numerical values associated with a time series analysis, a groundwater flow model, a geochemical model, and a nuclide transport model corresponding thereto, may be provided to a determined radioactive contamination restoration element through the external communication element 210.

Furthermore, in one embodiment, the central management element 220 may monitor groundwater characteristics in real time using a plurality of hydrogeochemical sensors disposed in an isolated section at each depth controlled by the multiple packers. In addition, the field management element of the field monitoring system 100 may be controlled to allow the positions of some of the multiple packers related to the displayed result of the display element 250 to flow away in a vertical direction.

The notification element 240 displays a predetermined notification when a result of the radioactive contamination evaluation corresponding to the analysis result is predicted as a contamination degree exceeding the reference range.

Figure 4:
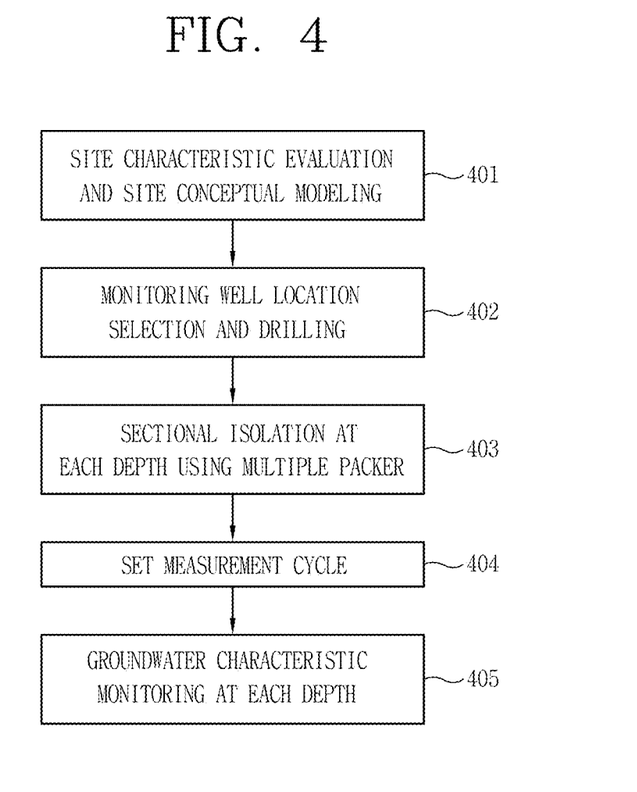
FIG. 4 is a flowchart for explaining a preparation process for monitoring groundwater characteristics at each depth in an integrated monitoring system for radiological surveillance of groundwater according to an embodiment of the present disclosure.

FIG. 4 is a flowchart for explaining a preparation process for monitoring groundwater characteristics at each depth in an integrated monitoring system for radiological surveillance of groundwater according to an embodiment of the present disclosure.

Referring to FIG. 4, site characteristics around a site to be monitored is evaluated to establish a site conceptual modeling (401). Next, based on the site conceptual modeling, the location and depth of monitoring wells are selected to drill the monitoring well (402). In addition, sectional isolation at each depth is performed using a multiple packer to carry out groundwater pressure, groundwater quality field measurement, radioactivity field measurement, and sampling at each depth of groundwater (403). Here, the sectional isolation 403 is carried out for a fractured section which can be a main flow path of groundwater, and hydraulic data values such as hydraulic conductivity and permeability coefficient are acquired in advance through a hydraulic test.

Then, a cycle of measurement may be set (404). Specifically, a measurement cycle according to the measurement optimization (improvement of an analytical sensitivity) of a field radioactivity measuring instrument (beta and gamma measuring instrument for water) is determined. At this time, an operation of a water pump including a measurement cycle, a collection cycle of measurement data, a groundwater collection cycle and a water collection amount, an external communication cycle, a laboratory analysis cycle, and the like may be set. Thereafter, the groundwater characteristics at each depth are monitored in real time (405).

Figure 5A:
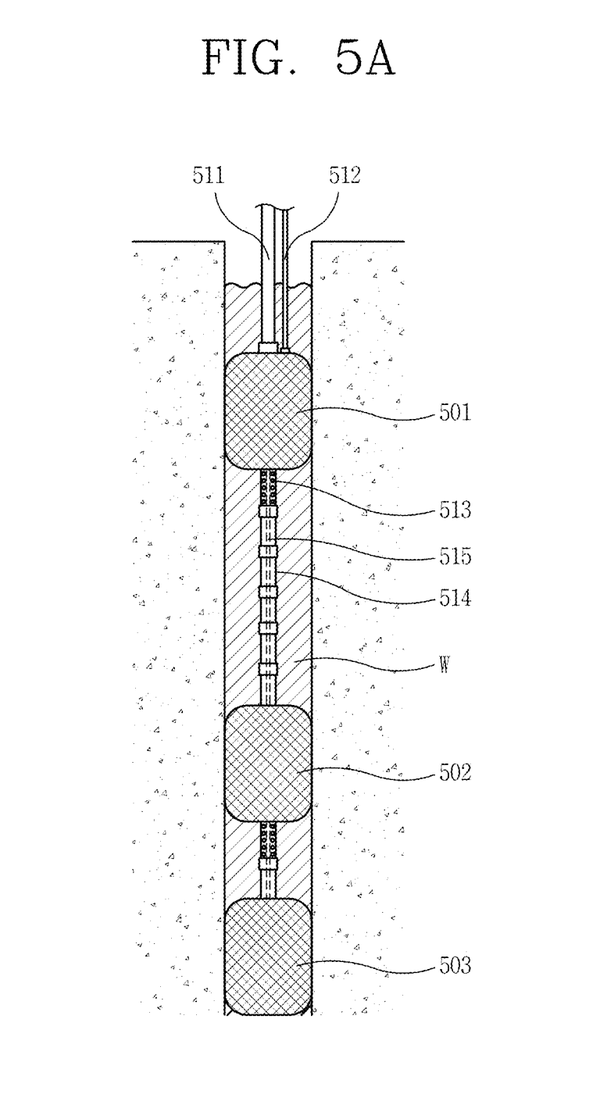
FIGS. 5A and 5B are views illustrating installation examples of a multiple packer system applied to an integrated monitoring system for radiological surveillance of groundwater according to an embodiment of the present disclosure.
Figure 5B:
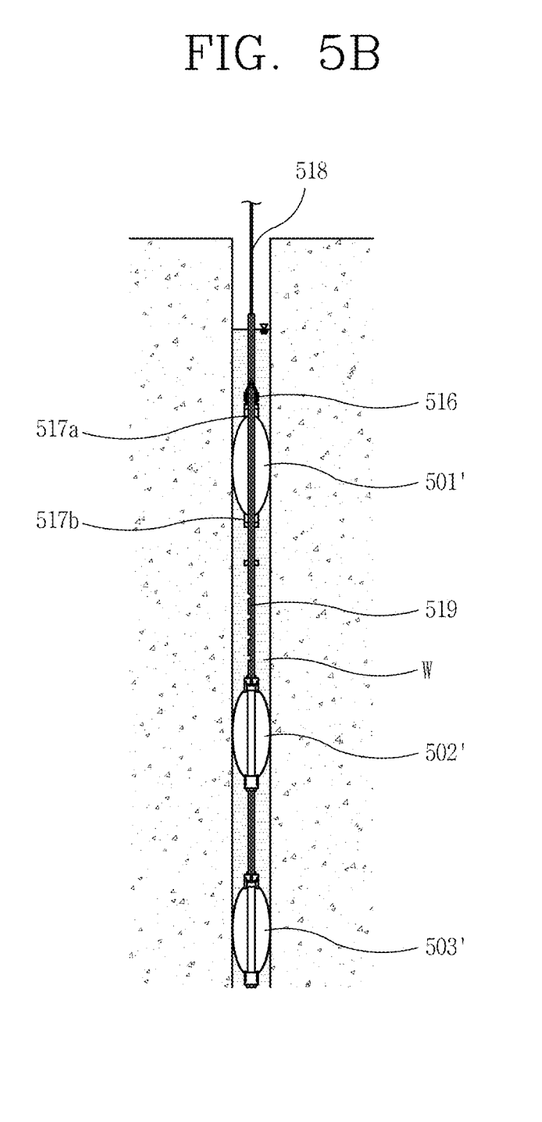

FIGS. 5A and 5B are views illustrating installation examples of a multiple packer system applied to an integrated monitoring system for radiological surveillance of groundwater according to an embodiment of the present disclosure.

The multiple packer system applied to the integrated monitoring system for radiological surveillance of groundwater according to the present disclosure may be established to form an isolated section of groundwater at each depth using a plurality of packers capable of flowing away in a vertical direction in a structure that surrounds each groundwater flow pipe disposed at multiple depths in groundwater.

Furthermore, in the present disclosure, the automatic branching apparatus connected to the groundwater flow pipe may be formed in a radial shape based on a central axis in which a plurality of groundwater inflow channels is formed to be rotatable with respect to each of the groundwater flow pipes at the multiple depths, thereby automatically branching the pumped groundwater.

At this time, the automatic branching apparatus may be made of, for example, stainless steel to prevent corrosion by groundwater. In addition, a plurality of groundwater inflow channels are respectively formed with a selection channel and a discharge channel to communicate with any one inflow channel selected by rotation to flow groundwater thereinto.

FIG. 5A as an example of multiple packers for establishing a multiple packer system may include at least a first packer 501, a second packer 502, a third packer 503 in a direction from top to bottom, and may be configured with supply pipes 511, 513 for supplying expansion fluid to the packers and applying a hydraulic pressure, a connection pipe 514 for connecting the packers, and a guide pipe 512 for guiding groundwater (W) existing between the packers to the outside. Furthermore, expansion fluid is supplied to the supply pipes 511, 513 to expand the packers at the same time to be brought into close contact with the monitoring well wall surface.

Next, referring to FIG. 5B, for another example of multiple packers for establishing a multiple packer system, the first packer 501' among the packers 501', 502', 503' is expanded by high-pressure fluid transferred through a pressure supply pipe 516 at an upper side from the pressure supply pipe 518 and brought into close contact with an outer circumferential surface of the monitoring well and a wall surface of the monitoring well. At this time, an upper moving cap 517a and a lower moving cap 517b may be provided on the upper portion and the lower portion of the first packer 501', respectively. Accordingly, the first packer 501' may flow away toward a lower perforated pipe 519 that transfers groundwater introduced into the upper or inner side thereof to the ground through the connection pipe or may be fixed to a current position. As a result, an isolated groundwater sampling section is formed between the first packer 501' and the other packers 502', 503'.

Accordingly, a multiple packer system capable of flowing away according to the present disclosure is established. On the other hand, the second packer 502' may be expanded by high-pressure fluid and closely fixed to the wall surface of the monitoring well, then the first packer 501' may move away in a vertical direction to a limiting ring (traverse ring) around the connection pipe, thereby easily adjusting a separation distance and space between the multiple packers. Therefore, the groundwater sampling section may be easily changed.

Figure 6A:
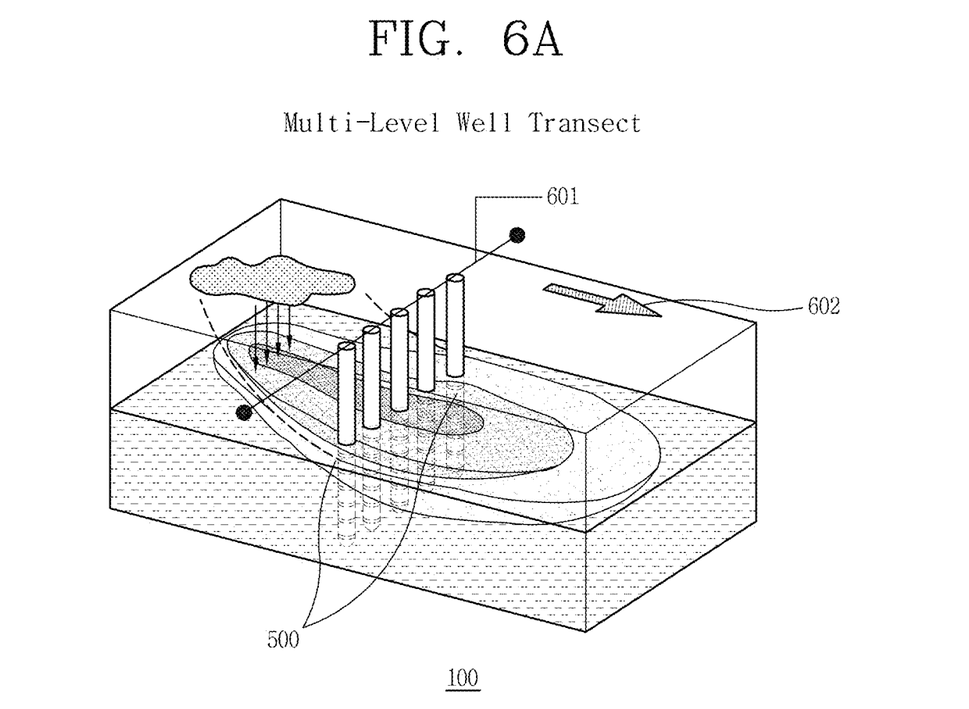
FIGS. 6A and 6B illustrate an example of monitoring radioactive contamination in groundwater using the multiple packer system of FIG. 5A or FIG. 5B, and an example of a contoured image of contaminant measurement values and contaminant distribution characteristics according to an analysis result of measurement data.

FIG. 6A is a view showing an example of monitoring radioactive contamination in groundwater using the multiple packer system of FIG. 5A or FIG. 5B.

The field monitoring system 100 includes a warehouse, which is a laboratory embedded with field monitoring system configurations including a monitoring well ground exposed section, and a multiple packer system installation monitoring well 500 within the warehouse.

The warehouse is a mobile laboratory having a size including a structure capable of loading a field monitoring system configuration section including the monitoring well ground exposed section thereinside, and an area capable of facilitating the work.

The size of the warehouse may be adjusted to be suitable for the user's implementation, but supplying power to drive the system is essential. Solar power supply should also be considered when power is not efficiently supplied. In addition, it is preferable to provide an air conditioner, a heater, and a dehumidifier so as to maintain the homeostasis irrespective of outside weather, thereby preventing the malfunction of the configuration system in advance. In addition, as a separation distance of each warehouse for surveillance decreases, the effect of the monitoring system may be increased, but the longitudinal direction may be preferably within about 100 m in consideration of the effect of an underground facility of the site.

The multiple packer system installation monitoring system 500 as a system of monitoring the groundwater characteristics (groundwater pressure, groundwater quality characteristics) of the groundwater at each depth may detect the groundwater characteristics at each depth in real time. Specifically, it may be possible to perform early diagnosis for a change of groundwater pressure and an inflow of contaminants, thereby enhancing the effect of contamination prevention. Sectional control at each depth is controlled by determining a main groundwater inflow section through the detailed investigation of a drill monitoring well and using a multiple packer for the relevant section. Furthermore, real-time groundwater characteristic monitoring may be performed by embedding various hydrogeochemical sensors (groundwater pressure, temperature, electric conductivity sensor, etc.) in each of the controlled sections.

Figure 6B:
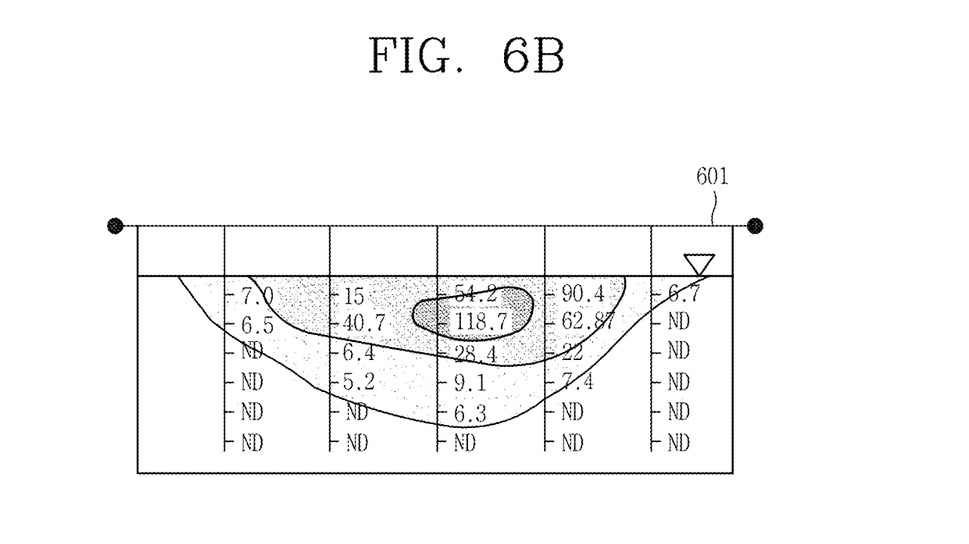

FIG. 6B is an exemplary view showing a contoured image of contaminant measurement values and contaminant distribution characteristics according to an analysis result of measurement data in an integrated monitoring system for radiological surveillance of groundwater according to an embodiment of the present disclosure. For example, FIG. 6B is a contoured image of the contaminant distribution characteristics when cut in a horizontal direction 601 (FIG. 6A) for connecting five monitoring wells in FIG. 6A.

The remote monitoring apparatus 200 displays a 3D contaminant plume based on the measurement of contaminants and the groundwater flow model. Here, in order to generate a 3D contaminant plume, a history of coordinate values changed in accordance with the update of the DB 250 (FIG. 3B) in the remote monitoring apparatus 200 is stored together with time information or in time order. The history of coordinate values stored in the DB 250 (FIG. 3B) may be generated as a three-dimensional stereoscopic image, and visualized as a contoured three-dimensional stereoscopic image through a known mapping technique, that is, displayed through a display element 230 (FIG. 3B). In other words the 3D contaminant plume may be visualized as a three-dimensional stereoscopic image that is contoured through a known mapping technique or displayed through the display element 230 (FIG. 3B). Through a contoured three-dimensional image, a position of contaminant source, nuclide transport and distribution characteristics, a predicted contamination range, a concentration, a flow and the like may be easily checked at a glance.

Figure 7:
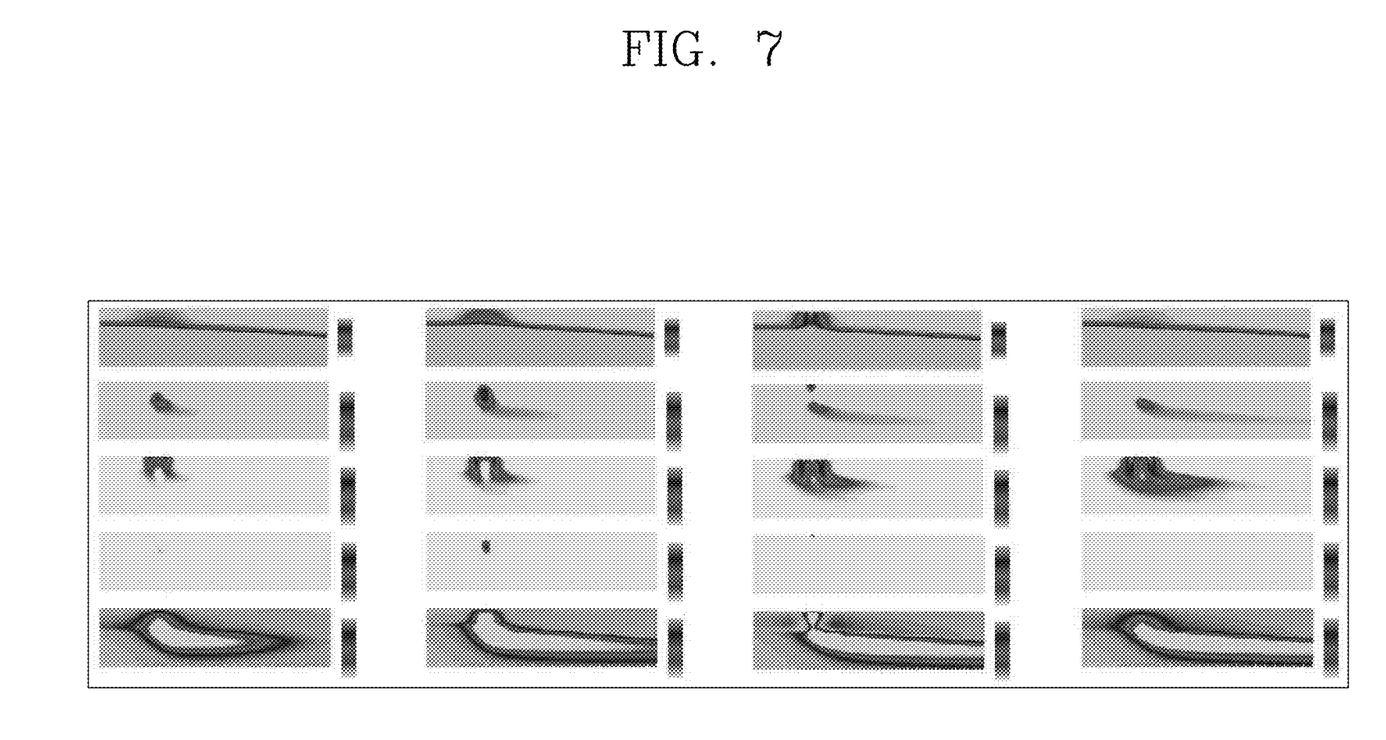
FIG. 7 is a view illustrating an example of a 2D graphical representation of a 3D graphic image of a nuclide transport model over time according to a monitoring result of an integrated monitoring system for radiological surveillance of groundwater according to an embodiment of the present disclosure.

FIG. 7 is a view illustrating a plurality of exemplary images of a 2D graphical representation of 3D graphic processing of a nuclide transport model over time according to a monitoring result of an integrated monitoring system for radiological surveillance of groundwater according to an embodiment of the present disclosure.

Such an image may be displayed as a three-dimensional image moving to correspond to a groundwater flow model (including a predicted advection rate of a contaminant plume depending on the flow direction and flow rate of groundwater) as time passes. In other words, it may be seen that a result of the contaminant plume measurement is not numerically displayed but provided in a graph format of the 3D contaminant plume. Through this, a flow direction, a flow rate, and the like of the contaminant plume over time may be visually intuitive.

In addition, in one embodiment, a groundwater flow model with characteristics modified by applying sensor values of various environmental sensors to a groundwater flow model may be established in real time to visualize a moving three-dimensional image being changed in a non-pattern shape according to the groundwater flow model with the modified characteristics. Accordingly, a restoration plan optimized at the point of restoration of radioactive contamination in groundwater may be established. At this time, it may be possible to change the scale and the reference position of a 3D contaminant plume corresponding to the three-dimensional image, or modify and display the attribute (e.g., color, pattern, etc.) of the corresponding three-dimensional image.

Furthermore, additionally, when the predicted advection rate of a 3D contaminant plume exceeds a reference value or a specific facility is located near the flow direction (for example, a hospital, etc.) or a dangerous nuclide is newly found, a preset alarm/warning may be displayed together with a three-dimensional image corresponding to the groundwater flow model. In addition, for this purpose, it may be possible to change the scale and the reference position of a 3D contaminant plume corresponding to the three-dimensional image, or modify and display the attribute (e.g., color, pattern, etc.) of the corresponding three-dimensional image.

As described above, the integrated monitoring system for radiological surveillance of groundwater according to the present disclosure may automate DB collection, data transmission, data analysis and visualization to maximize the efficiency of manpower and expense, and provide an alarm system for malfunctioning of equipment and calculation of non-ideal data and remotely control the field system to implement the integration and automation of the groundwater radioactive contamination monitoring system. Moreover, a groundwater three-dimensional flow model of groundwater using a monitoring basis of groundwater at multiple depths may be established to detect the hydrogeochemical characteristics and radioactivity distribution of groundwater in real time at each depth and allow an early diagnosis of contaminants inflow and outflow. Besides, a change in contaminant source prediction, behavior, nuclide distribution characteristics, concentration, flow and the like may be visualized and provided as a moving three-dimensional image to allow the user to easily detect the contamination degree at a glance, thereby providing convenience automatically used for a monitoring measurement cycle and automatically referenced for restoration plan establishment.

The foregoing present disclosure may be implemented as codes readable by a computer on a medium written by the program. The computer-readable media may include all kinds of recording devices in which data readable by a computer system is stored. Examples of the computer-readable media may include ROM, RAM, CD-ROM, magnetic tape, floppy disk, and optical data storage device, and the like, and also include a device implemented in the form of a carrier wave (for example, transmission via the Internet).

The detailed description thereof should not be construed as restrictive in all aspects but considered as illustrative. The scope of the invention should be determined by reasonable interpretation of the appended claims and all changes that come within the equivalent scope of the invention are included in the scope of the invention.

What is claimed is:

1. An integrated monitoring system for radiological surveillance of groundwater around a nuclear facility, comprising:
   a field monitoring system configured to monitor sectionally isolated groundwater characteristics by establishing a multiple packer system at each depth in groundwater around the nuclear facility, and measure whether or not radioactive contamination has occurred at each depth in groundwater pumped through an automatic branching apparatus connected to a sectional groundwater flow pipe isolatedly disposed at the each depth, and convert field measurement data acquired based on the measurement result into a database and transmit the database to a remote monitoring apparatus over a network; and
   the remote monitoring apparatus configured to remotely control the field monitoring system, and receive the database-based field measurement data from the field monitoring system, and analyze the received field measurement data to predict a radioactive contaminant source, and provide a contaminant plume showing the distribution characteristics of contaminants in 3D graphic processing; and
   whererin the remote monitoring apparatus transmits a monitoring procedure input value based on at least one of a range of radioactive contamination, a concentration, a groundwater flow, and a nuclide transport included in the 3D graphic to the field monitoring system, and
   whererin the field monitoring system measures the radioactive contamination occurred at each depth in groundwater by changing a at least one of a radioactive measurement cycle of groundwater for each section, a collection cycle of measurement data, a groundwater collection cycle and a water collection amount according to the monitoring procedure input value.

2. The integrated monitoring system for radiological surveillance of groundwater of claim 1, wherein the integrated monitoring system for radiological surveillance of groundwater further comprises an external communication element for communication between the field monitoring system and the remote monitoring apparatus, and the external communication element comprises a plurality of communication network elements to prevent the loss of data to receive the database-based field measurement data at a planned communication cycle using any one of the plurality of communication network elements, and transmit the monitoring procedure input value to the field monitoring system as a feedback using another one thereof.

3. The integrated monitoring system for radiological surveillance of groundwater of claim 1, wherein the remote monitoring apparatus further comprises:

an input element configured to receive a time setting information related to the 3D graphic; and a display element configured to display the 3D graphic and a predictive three-dimensional image in which an image of the 3D graphic gradually changes according to the received time setting information.

4. The integrated monitoring system for radiological surveillance of groundwater of claim 3, wherein a range of radioactive contamination, a concentration, a groundwater flow, and a nuclide transport in groundwater are displayed in a form of a combined image on the 3D graphic.

5. The integrated monitoring system for radiological surveillance of groundwater of claim 1, wherein the remote monitoring apparatus provides data concerning the 3D graphic and numerical values associated with a time series analysis, a groundwater flow model, a geochemical model, and a nuclide transport model corresponding thereto to a determined radioactive contamination restoration element through an external communication element based on a radioactive contamination evaluation corresponding to an analysis of the received field measurement data.

6. The integrated monitoring system for radiological surveillance of groundwater of claim 1, wherein the remote monitoring apparatus further comprises a notification element configured to display a predetermined notification when a result of radioactive contamination evaluation corresponding to an analysis of the field measurement data is predicted as a contamination degree exceeding the reference range.

7. The integrated monitoring system for radiological surveillance of groundwater of claim 1, wherein the multiple packer system is established to form an isolated section of groundwater at each depth using a plurality of packers capable of flowing away in a vertical direction with a structure that surrounds each groundwater flow pipe disposed at each depth, and an automatic branching apparatus connected to the groundwater flow pipe is formed in a radial shape based on a central axis in which a plurality of groundwater inflow channels are formed to be rotatable with respect to each of the groundwater flow pipes at each depth to automatically branch the pumped groundwater for each section.

8. The integrated monitoring system for radiological surveillance of groundwater of claim 7, wherein the remote monitoring apparatus performs groundwater characteristic monitoring in real time using a plurality of hydrogeochemical sensors disposed in an isolated section at each depth controlled by the plurality of packers, and controls the field monitoring system to change a survey cycle and order of some depths related to a display result of the depths isolated by the plurality of packers.

9. A method of operating an integrated monitoring system for radiological surveillance of groundwater comprising a field monitoring system around a nuclear facility and a remote monitoring apparatus that controls the field monitoring system, the method comprising:

monitoring sectionally isolated groundwater characteristics by establishing a multiple packer system at each depth in groundwater around the nuclear facility;

measuring whether or not radioactive contamination of groundwater has occurred for the each section through an automatic branching apparatus connected to a groundwater flow pipe isolatedly disposed for the each section;

converting field measurement data acquired on the basis of the measurement result into a database and transmitting the database to the remote monitoring apparatus over a network;

analyzing the database-based field measurement data from the field monitoring system to predict a radioactive contaminant source;

displaying a contaminant plume showing the distribution characteristics of contaminants in 3D graphic processing;

transmitting a monitoring procedure input value based on at least one of a range of radioactive contamination, a concentration, a groundwater flow, and a nuclide transport included in the 3D graphic to the field monitoring system, and measuring the radioactive contamination occurred at each depth in groundwater by changing a at least one of a radioactive measurement cycle of groundwater for each section, a collection cycle of measurement data, a groundwater collection cycle and a water collection amount according to the monitoring procedure input value.

* * * * *